(12) United States Patent
Jung et al.

(10) Patent No.: US 8,529,436 B2
(45) Date of Patent: Sep. 10, 2013

(54) ENDOSCOPE, ENDOSCOPE SYSTEM HAVING THE SAME AND ENDOSCOPE CONTROL METHOD

(75) Inventors: Han Jung, Daejeon (KR); Byung-Hyuk Kim, Daejeon (KR); Yong-Woo Lee, Daejeon (KR); Chul Cha, Daejeon (KR); Sung-Do Kim, Daejeon (KR)

(73) Assignee: i3System Corp. (KR)

( * ) Notice: Subject to any disclaimer, the term of this patent is extended or adjusted under 35 U.S.C. 154(b) by 877 days.

(21) Appl. No.: 12/634,056

(22) Filed: Dec. 9, 2009

(65) Prior Publication Data

US 2010/0185051 A1    Jul. 22, 2010

(30) Foreign Application Priority Data

Jan. 16, 2009    (KR) .................. 10-2009-0003846

(51) Int. Cl.
*A61B 1/00*       (2006.01)
*A61B 1/04*       (2006.01)

(52) U.S. Cl.
USPC .......................................... 600/117; 600/118

(58) Field of Classification Search
USPC .................. 600/103, 109, 117, 118, 160
See application file for complete search history.

(56) References Cited

U.S. PATENT DOCUMENTS

| | | | |
|---|---|---|---|
| 2003/0092964 A1* | 5/2003 | Kim et al. | 600/101 |
| 2003/0216622 A1* | 11/2003 | Meron et al. | 600/300 |
| 2005/0036059 A1* | 2/2005 | Goldwasser | 348/373 |
| 2006/0004276 A1* | 1/2006 | Iddan et al. | 600/407 |
| 2006/0004285 A1* | 1/2006 | Meron et al. | 600/424 |
| 2007/0100200 A1* | 5/2007 | Suzuki et al. | 600/101 |
| 2007/0100208 A1* | 5/2007 | Lewkowicz et al. | 600/160 |
| 2007/0106112 A1* | 5/2007 | Gat et al. | 600/109 |
| 2007/0221233 A1* | 9/2007 | Kawano et al. | 128/899 |
| 2007/0270628 A1* | 11/2007 | Kawano et al. | 600/12 |
| 2009/0281387 A1* | 11/2009 | Takizawa et al. | 600/117 |

* cited by examiner

*Primary Examiner* — Philip R Smith
(74) *Attorney, Agent, or Firm* — Ostrolenk Faber LLP

(57) ABSTRACT

An endoscope, an endoscope system having an endoscope, and an endoscope control method are disclosed. The endoscope includes: a main body and a buoyancy control device. The main body may be configured in the form of a capsule and include an image capturing unit for capturing image information. The buoyancy control device may control buoyancy by changing the volume of the main body. Images of various types of internal organs can be precisely captured.

11 Claims, 8 Drawing Sheets

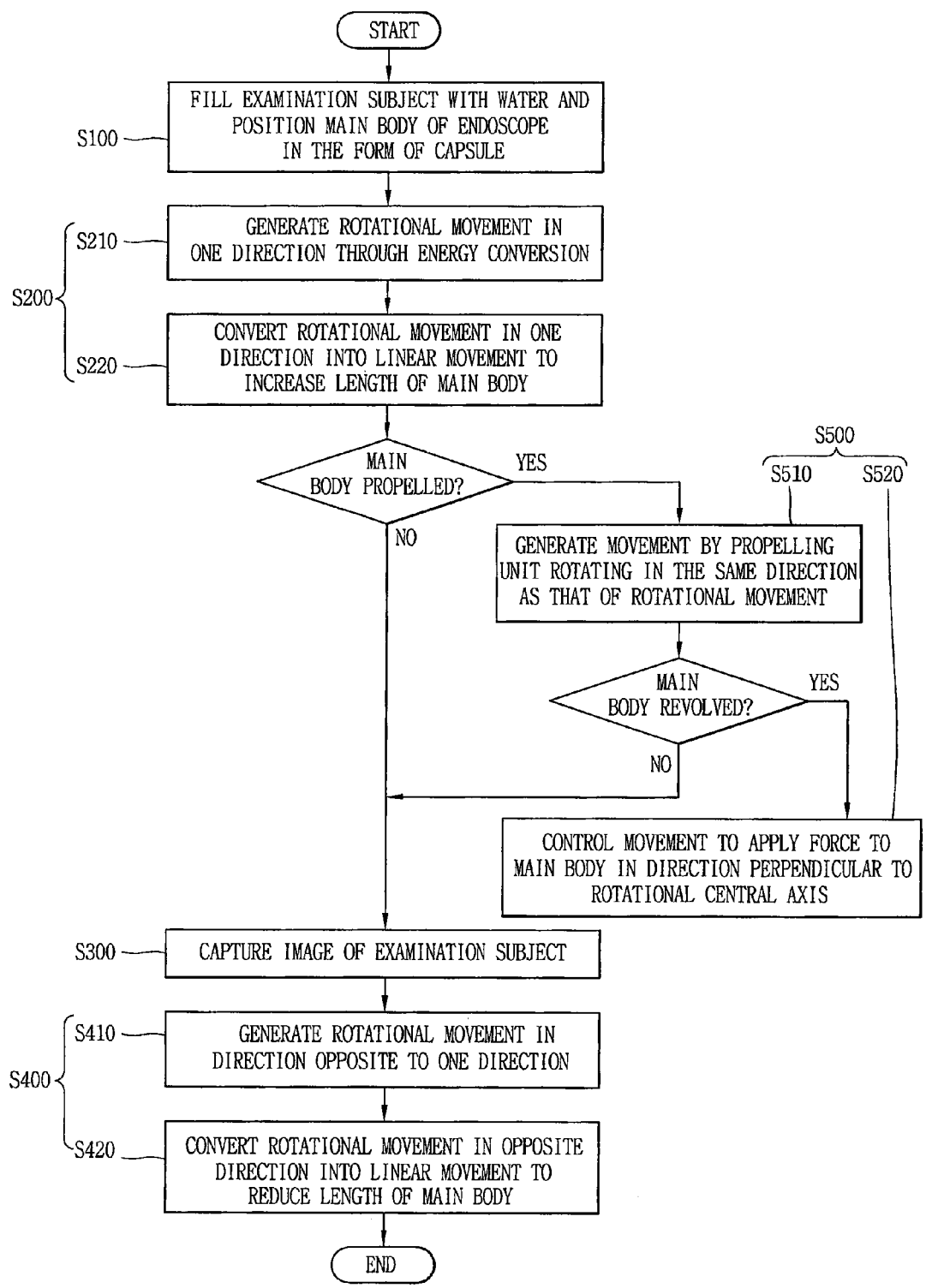

US 8,529,436 B2

ENDOSCOPE, ENDOSCOPE SYSTEM HAVING THE SAME AND ENDOSCOPE CONTROL METHOD

CROSS-REFERENCE TO RELATED APPLICATION

Pursuant to 35 U.S.C. §119(a), this application claims the benefit of earlier filing date and right of priority to Korean Application No. 10-2009-0003846, filed on Jan. 16, 2009, the contents of which is incorporated by reference herein in its entirety.

BACKGROUND OF THE INVENTION

1. Field of the Invention

The present invention relates to an endoscope for capturing image information of internal organs of human beings or animals.

2. Description of the Related Art

In the past, the internal organs of human beings or animals cannot be viewed without an operation or autopsy. However, devices for allowing for direct viewing of lesion in the internal organs or body cavities have been devised in line with the advancement of medical and scientific technologies, and an endoscope is one of those devices.

Among the endoscopes, a camera-type endoscope that directly inserts a camera into an internal organ or a fiberscope-type endoscope using glass fiber, and the like, are commonly used. However, the camera-type endoscope or the fiberscope-type endoscope causes pain and nausea of a person in an examination, and cannot capture an image of a small intestine, having a restriction in their use. In addition, the camera-type endoscope or the fiberscope-type endoscope has a disadvantage in that it can hardly examine the digestive organs such as the small intestine or the like.

Recently, new attempts are being made by hardware or software in developing the endoscope techniques.

In addition to such attempts, an endoscope which may have the form of a capsule so as not to make a patient feel inconvenient or pain and be able to examine various types of internal organs, and an endoscope control method are required.

SUMMARY OF THE INVENTION

Therefore, in order to address the above matters, the various features described herein have been conceived.

An aspect of the present invention provides an endoscope capable of preventing an examination subject (i.e., person to be examined) from feeling pain or reducing pain the examination subject may feel and allowing an inspector to control it, and an endoscope system, and an endoscope control method.

Another aspect of the present invention provides an endoscope capable of precisely capturing an image of an internal organ.

According to an aspect of the present invention, there is provided an endoscope including a main body and a buoyancy control device. The main body may be configured in the form of a capsule and include an image capturing unit for capturing image information. The buoyancy control device may control buoyancy by changing the volume of the main body.

According to an aspect of the present invention, there is provided an endoscope system including: an endoscope and a controller. The controller may be formed to control the endoscope. The endoscope system may further include a chair allowing the examination subject to sit thereon. The chair may be formed to be rotatable with respect to axes perpendicular to each other. The endoscope system may further include a reception pad configured to receive a signal transmitted from the endoscope. The reception pad may be attached to a front surface and a rear surface of the examination subject.

The buoyancy control device may include a driving unit configured to have a driving shaft rotating in an axial direction. The buoyancy control may include first and second cases connected to be relatively movable with each other according to a rotation of the driving shaft. One of the first and second cases may be inserted into another, and the driving shaft may be connected with the second case to allow the second case to be rotated. The buoyancy control device may be configured to change the rotation of the second case into a linear movement in a direction in which the first case is inserted.

A protrusion pin may be formed on an outer circumference of the second case. An insertion recess into which the protrusion pin is inserted may be formed on an inner circumference of the first case. At least a portion of the insertion recess may be sloped with respect to the rotational central axis of the second case. The insertion recess may include first and second rotary recesses and a connection recess. The first and second rotary recesses may be formed in a circumferential direction of the first case to allow the protrusion pin to be rotated continuously, and disposed to be spaced apart. The connection recess may connect the first and second rotary recesses and be formed in a spiral direction of the first case. The portion where the first and second rotary recesses and the connection recess cross may be formed to change a movement path of the protrusion pin according to the rotational direction of the driving shaft.

The endoscope may further include a gyration device mounted at the main body. The gyration device may be formed to revolve the main body. The gyration device may include a propulsion unit and a protection unit. The propulsion unit may be connected to the driving shaft and may be formed to propel the main body through rotation. The protection unit may be formed to accommodate the propulsion unit. The protection unit may include a plurality of through holes connecting the space in which the propulsion unit is installed with the exterior. The plurality of through holes may be disposed to be asymmetrical to the driving shaft.

According to another aspect of the present invention, there is provided an endoscope control method. The endoscope control method includes: positioning a main body; swelling a volume; capturing an image; and reducing the volume. In positioning the main body, an examination subject may be filled with water, and the main body of the endoscope in the form of a capsule is positioned at the examination subject. In swelling the volume, the volume of the main body of the endoscope in the form of a capsule is swelled to increase the buoyancy. In capturing an image, an image of an examination subject is captured. In reducing the volume, the volume of the main body is reduced.

The swelling and reducing of the volume may include: generating a rotational movement; and varying a length. In generating a rotational movement, the rotational movement is generated through an energy conversion. In varying a length, the length of the main body is varied by converting a rotational movement into a linear movement.

The endoscope control method may further include: revolving the main body. In revolving the main body, the main body is propelled, and then, a force is applied in a direction perpendicular to the propelling direction to revolve the main body. The revolving of the main body may include: generating a water flow; and controlling the water flow. In generating the water flow, the water flow is generated by a propulsion unit rotating in the same direction as the rotational movement. In controlling the water flow, the water flow is controlled to apply a force to the main body in a direction perpendicular to a rotational central axis.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 4a and 4b are flow charts illustrating the process of an endoscope control method according to an exemplary embodiment of the present invention;

FIG. 6 is a conceptual view showing the principle of a kinetic conversion of a buoyancy control device of FIG. 5a;

FIG. 8 is a conceptual view of an operation of a gyration device of FIG. 5a.

DETAILED DESCRIPTION OF THE INVENTION

Figure 1:
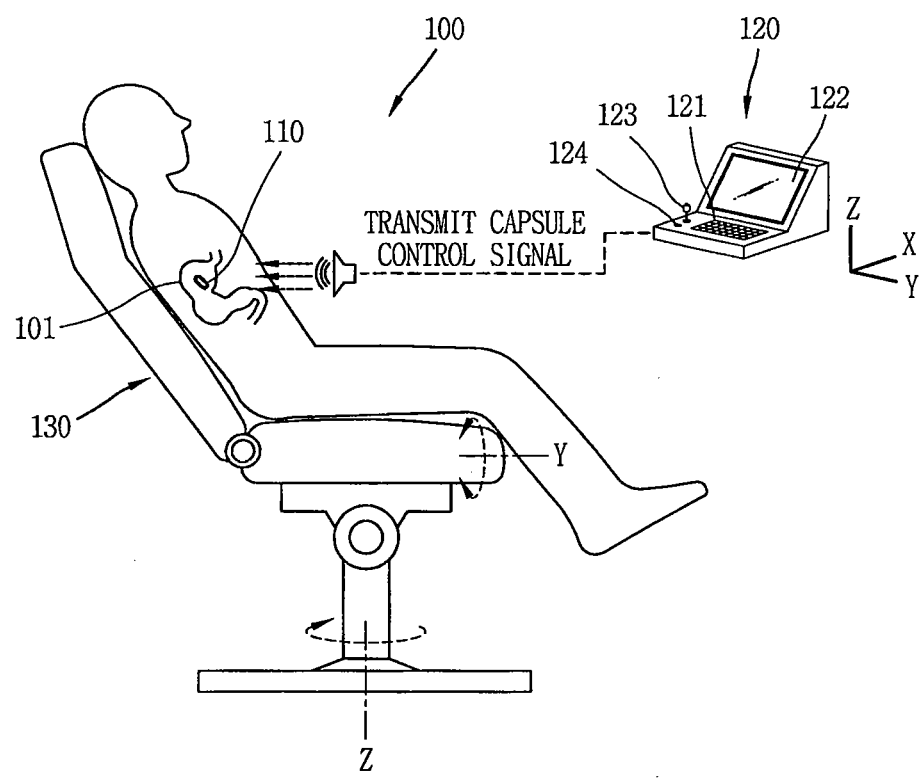
FIG. 1 is a conceptual view showing an endoscope system operating for an endoscope examination according to an exemplary embodiment of the present invention.

An endoscope, an endoscope system having an endoscope, and an endoscope control method according to exemplary embodiments of the present invention will now be described with reference to the accompanying drawings. For the same elements and equivalents to those shown in the figures and in the description, the same or like reference numerals are used and a corresponding detailed explanation is omitted merely for the sake of convenience. As used herein, the singular forms are intended to include the plural forms as well, unless the context clearly indicates otherwise.

Figure 2:
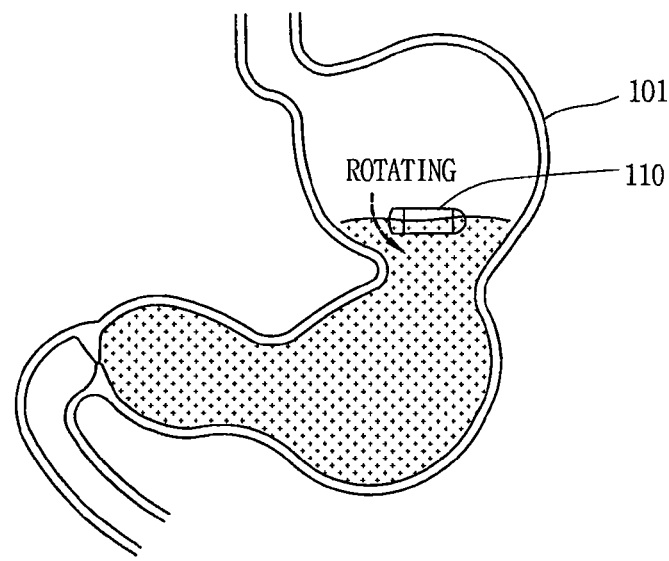
FIG. 2 is a conceptual view showing the endoscope of FIG. 1 located in an examination subject.

FIG. 1 is a conceptual view showing an endoscope system operating for an endoscope examination according to an exemplary embodiment of the present invention, and FIG. 2 is a conceptual view showing the endoscope of FIG. 1 located in an examination subject.

An endoscope 110 has such a form that can be positioned in an internal organ of human beings or animals, an examination subject. For example, the endoscope 110 may be configured in the form of a capsule. With reference to FIGS. 1 and 2, the examination subject may include a stomach 101 having a relatively large volume among digestive organs.

With reference to FIG. 2, water is filled in the stomach 101, and the endoscope 110 is positioned in the water. The buoyancy may be increased to make the endoscope 110 disposed on the water. In the following description, it is illustrated that the stomach is filled with water, but the present invention is not necessarily limited thereto. That is, the stomach 101 may be filled with various types of fluids, e.g., a liquid medicine or the like, instead of water.

The endoscope 110 includes an image capturing unit 111 (See FIG. 5a) for capturing image information. An image of the interior of the stomach 101 can be captured through the image capturing unit 111, from which lesion of the stomach 101 may be checked.

With reference to FIG. 1, an endoscope system 100 includes a controller 120 configured to control the endoscope 110.

The controller 120 is configured to transmit a signal for controlling the operation of the endoscope 110 to the endoscope 110. The controller 120 may be configured to store and read the captured image in real time. The controller 120 may include a user input unit 121, a monitor 122, and the like.

The user input unit 121 may be configured to allow a user to input information corresponding to the control signal. The monitor 122 may be configured to display image information corresponding to the control signal.

The endoscope system 100 includes a chair 130 on which the examination subject may sit.

The chair 130 may be formed to be rotated with respect to axes X, Y, and Z which are perpendicular to each other. The rotation may be implemented by a driving motor, through a hinge coupling, and the like. For example, hinge couplings, namely, couplings rotatable with respect to the axes X, Y, and Z are formed at a lower end portion of the chair 130, and driving motors rotatable with respect to the axes X, Y, and Z can be mounted at the hinge couplings.

The controller 120 may include an adjusting unit 123 for controlling the rotation with respect to the axes X, Y, and Z. The chair 130 may be formed to be rotated in the three axes X, Y, and Z according to a movement of the adjusting unit 123.

The structure in which the chair 130 and the adjusting unit 123 correspond to each other will now be described. The adjusting unit 123 is formed such that its free end is movable in the X axis direction or in the Y axis direction. As the free end of the adjusting unit 123 is moved in the X and Y axes direction, the chair 130 is rotated based on the X axis direction or the Y axis direction A rotationally movable button 124 may be disposed to be adjacent to the adjusting unit 123. When the rotationally movable button 124 is pressed and the free end of the adjusting unit 123 is moved in the X axis direction or in the Y axis direction, the chair 130 may be rotated based on the Z axis.

The endoscope system 100 including the chair 130 can capture various images of the stomach 101 at different angles as the angle of the chair 130 is controlled in the three axes.

Figure 3:
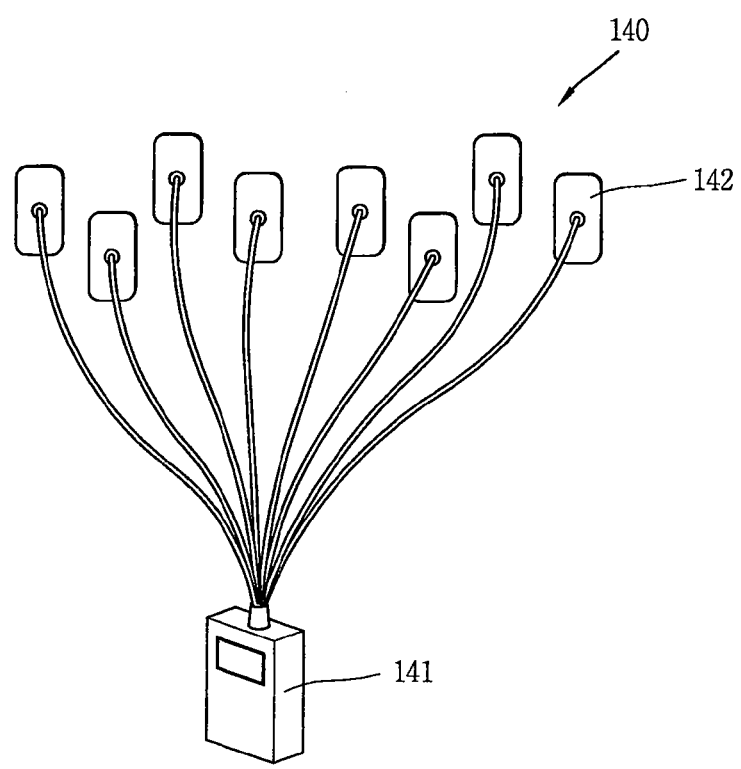
FIG. 3 is a conceptual view showing a reception device configured to receive image information transmitted from the endoscope of FIG. 1.

FIG. 3 is a conceptual view showing a reception device configured to receive image information transmitted from the endoscope of FIG. 1;

The reception device 140 includes a receiver 141 and a reception pad 142.

The reception pad 142 is configured to receive a signal transmitted from the endoscope 110. The signal may be a signal corresponding to image information obtained by capturing images of the stomach 101, operation information of the endoscope 110, and the like.

The reception pad 142 may be attached to the body of the examination subject. With reference to FIG. 3, a plurality of reception pads 142 are provided so as to be attached to a front surface or a rear surface of the body of the examination subject. Thus, the reception pads 142 can smoothly receive a signal transmitted from the endoscope 110 in every direction.

The receiver 141 may be configured to process a signal which has been received by the reception pads 142. For example, the reception pads may be electrically connected to the receiver 141 and convert the signal into information corresponding to the signal.

Figure 4A:
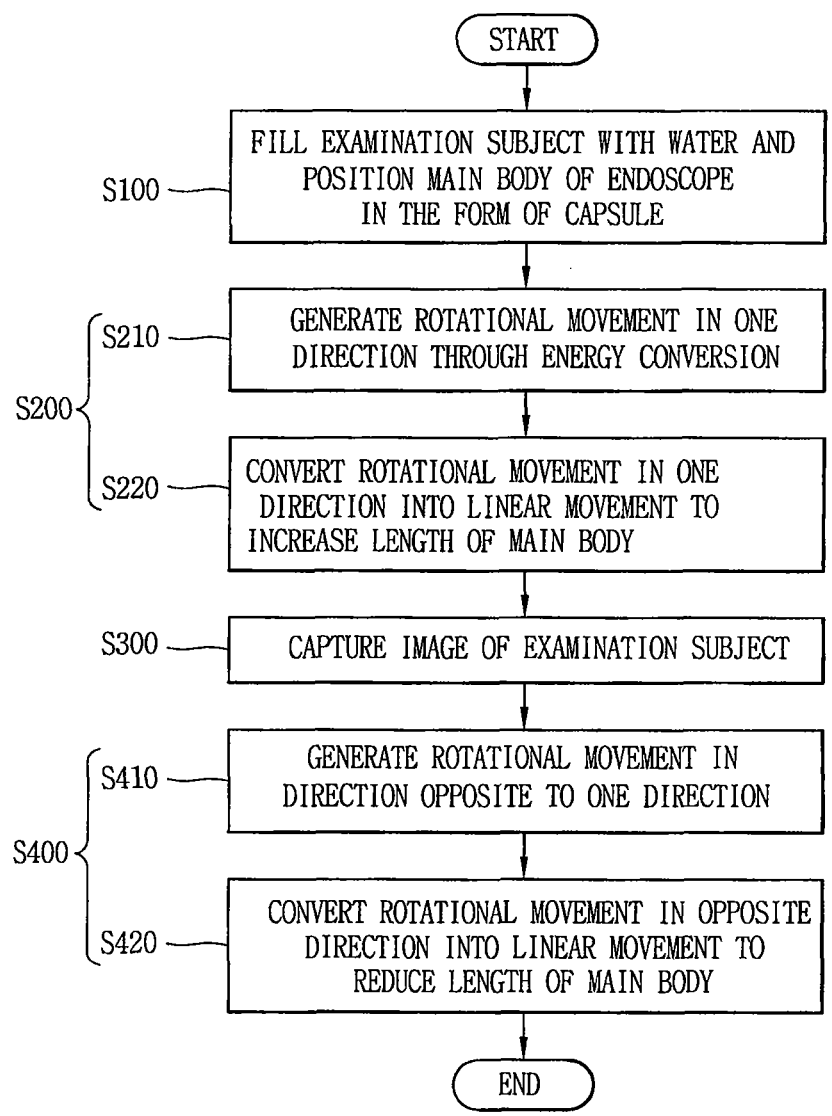

FIGS. 4a and 4b are flow charts illustrating the process of an endoscope control method according to an exemplary embodiment of the present invention.

According to the endoscope control method, first, the examination subject is filled with water, and the main body of the endoscope in the form of a capsule is then placed in the water (S100). This is performed as the examination subject drinks water and swallows the endoscope.

With reference to FIG. 4a, in step S200 of swelling the volume of the endoscope, the volume of the main body of the endoscope is swelled, according to which the buoyancy of the endoscope increases. The step S200 of swelling the volume may include step S210 of generating a rotational movement and step S220 of varying a length.

In the step S210 of generating a rotational movement, the rotational movement is generated through energy conversion. For example, a driving unit configured to have a driving shaft rotated in an axial direction and a battery are mounted at the main body. Electric energy of the battery is converted into kinetic energy by the driving unit. The driving unit may be, for example, an electric motor.

In the step S220 of varying the length, the length of the main body is varied by changing a rotational movement into a linear movement. For example, the main body includes the first and second cases, and if the driving shaft is rotated in one direction, the first and second cases are connected to be relatively moved with each other in a direction in which the length of the main body increases.

As the length of the main body increases, the volume of the main body swells to increase the buoyancy. The increase in the buoyancy makes the endoscope float on the water filled in the stomach 101.

When the endoscope floats on the water, an image of the examination subject is captured (S300). The examination subject may be, for example, the stomach walls.

As the water within the stomach 101 digests, the endoscope, which has started to capture the image of the upper stomach walls, gradually goes down to capture an image of the lower stomach walls.

When the capturing of the images of the stomach is finished, the volume of the main body is reduced (S400). The reducing of the volume (S400) may include generating a rotational movement (S410) and varying the length (S420).

In step S410 of generating a rotational movement, a rotational movement is generated in a direction opposite of that of the rotation in step S200 of swelling the volume of the main body through energy conversion. In step S420 of varying the length, the rotational movement in the opposite direction is converted into a linear movement to reduce the length of the main body. The volume-reduced endoscope is naturally discharged to the outer side along the digestive organs.

With reference to FIG. 4b, the endoscope control method may further include revolving the main body (S500). In step (S500) of revolving the main body, the main body is propelled and then a force is applied in a direction perpendicular to the propelling direction to revolve the main body. For example, in step S500 of revolving the main body, the force to be applied to the direction of a rotational central axis of the rotational movement and the force to be applied in the direction perpendicular to the rotational central axis are generated to revolve the main body.

The step S500 of revolving may include generating a water flow (S510) and controlling the water flow (S520).

In step S510 of generating the water flow, the water flow is generated by a propelling unit which rotates in the same direction as that of the rotational movement. The propelling unit may be, for example, a propeller. As shown, the driving of the propelling unit may be performed as the inspector chooses to propel the main body. Focusing of the image being captured may be adjusted by propelling the main body.

In controlling the water flow (S520), the water flow is controlled such that a force is applied to the main body in a direction perpendicular to the rotational central axis.

For example, a protection unit formed to accommodate the propelling unit therein is mounted on the main body. The protection unit in which the propelling unit is installed includes a plurality of through holes which are asymmetrically disposed to the driving shaft. The space of the protection unit in which the propelling unit is installed is connected with the exterior through the plurality of through holes.

The water within the stomach is introduced into the propelling unit through some of the through holes and then discharged from the propelling unit through other through holes, making a water flow. Because the through holes are asymmetrically disposed, the water flow applies a force to the main body in the direction perpendicular to the rotational central axis, and accordingly, the main body is revolved. By controlling the propelling and revolving of the main body, the images of the stomach can be more precisely captured.

As illustrated, whether to revolve the main body may be made according to the inspector's selection. For example, whether to revolve the main body may be determined according to a rotational speed of the propelling unit. If the rotational speed of the propelling unit is reduced, the force for revolving the main body becomes weak, propelling the main body in the linear direction. If the rotational speed of the propelling unit is increased, the force for revolving the main body becomes strong, revolving the main body.

Figure 5A:
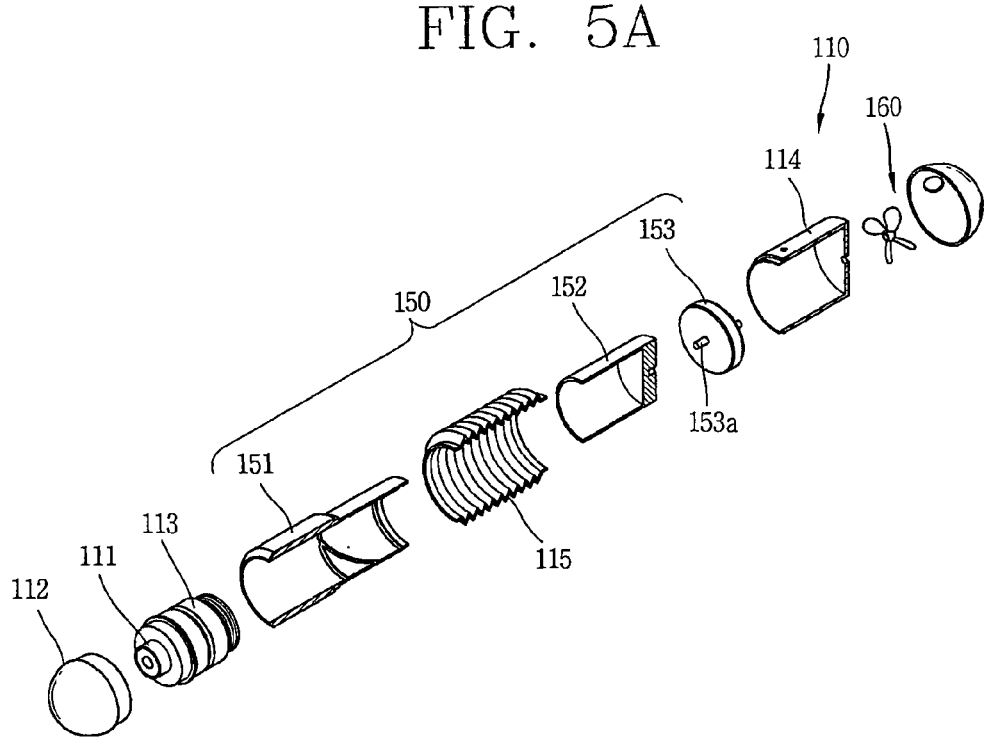
FIGS. 5a and 5b are an exploded perspective view and an exploded sectional view of the endoscope of FIG. 1, respectively.
Figure 5B:
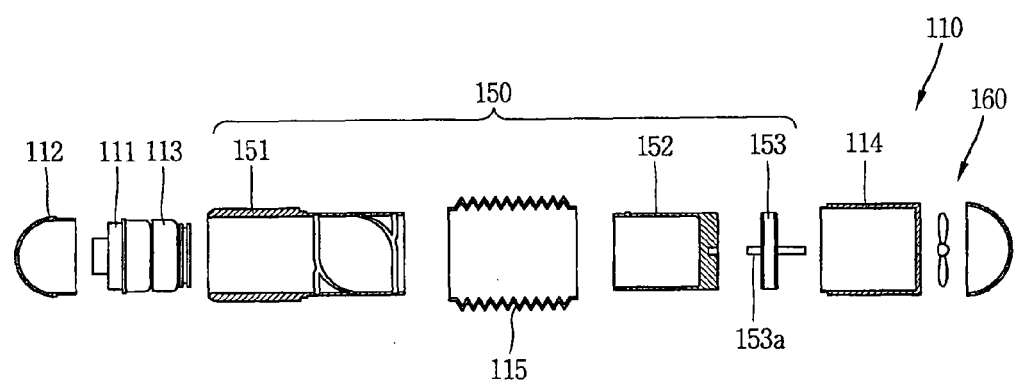

The endoscope implementing the endoscopy by the endoscope control method will now be described. FIGS. 5a and 5b are an exploded perspective view and an exploded sectional view of the endoscope of FIG. 1, respectively.

An image capturing unit 111 and an image capturing protection unit 112 are mounted on the main body of the endoscope 110.

The image capturing unit 111 may be, for example, a camera module. The image capturing protection unit 112 accommodates the image capturing unit 111 to protect the image capturing unit, which is then mounted on the main body. As illustrated, the image capturing protection unit 112 may have a dome shape. The image capturing protection unit 112 may be made of a light-transmissive material.

A battery 113 is disposed adjacent to the image capturing unit 111. The battery 113 supplies electrical energy to the image capturing unit 111. The battery 113 may be rechargeable.

The buoyancy control device 150 includes first and second cases 151 and 152, and a driving unit 153.

The image capturing unit 111 and the battery 113 are installed at one side of the first case 151 constituting the external appearance of the main body. The second case 152 is connected to the other side of the first case 151 such that they can be relatively movable with each other.

The second case 152 is connected with the driving unit 153. The driving unit 153 is electrically connected with the battery 113. The driving unit 153 includes a driving shaft 153a formed to be rotated in an axial direction. The driving to unit 153 may be, for example, an electrical motor, and converts electric energy into rotational kinetic energy. The driving unit 153 is formed such that it can rotate the driving shaft 153a in both directions.

The second case 152 and the driving unit 153 are installed in a third case 114. The third case 114 and the second case 152 are separately disposed so that they cannot be in frictional contact with each other.

The first and second cases 151 and 152 may be formed to be relatively moved with each other according to the rotation of the driving shaft 153a.

One of the first and second cases 151 and 152 is inserted into the other. With reference to the drawings, the second case 152 is inserted into the first case, and the driving shaft 153a is connected with the second case 152 to rotate the second case 152.

The buoyancy control device 150 is formed to convert the rotation of the second case 152 into a linear movement in a direction in which the first case 151 is inserted. The first and second cases 151 and 152 may be formed such that their insertion degree varies depending on the linear movement.

The first and second cases 151 and 152 are covered by a protection case 115. The protection case 115 may be made of an elastic material that can be flexible according to a change in the insertion degree of the first and second cases 151 and 152. As shown, the protection case 115 may have a plurality of creases to improve the elasticity.

A control unit (not shown) may be formed within the main body. For example, the control unit may have a form of a circuit board. The control unit may be formed to transmit and receive a signal to and from the controller 120 (See FIG. 1). The control unit may be formed to control the rotational speed and rotational direction of the driving shaft 153a. The control unit may be formed to control the image capturing unit 111.

Figure 6:
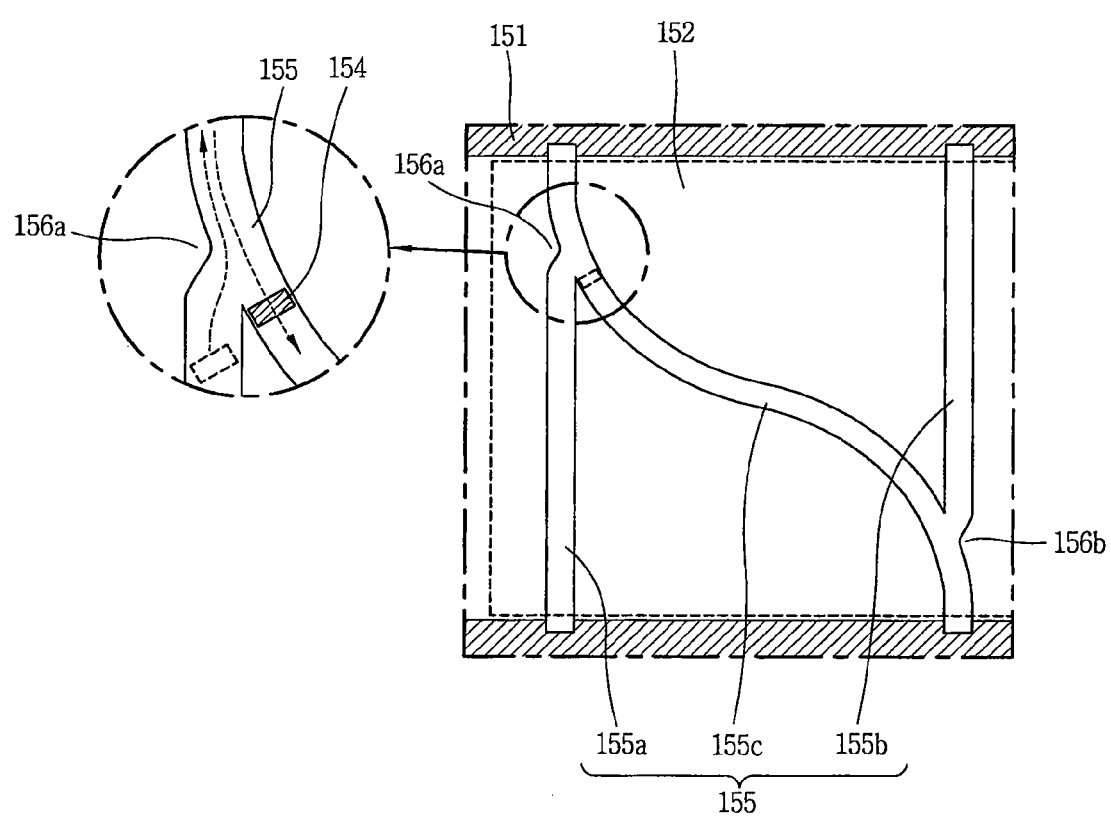
Figure 7A:
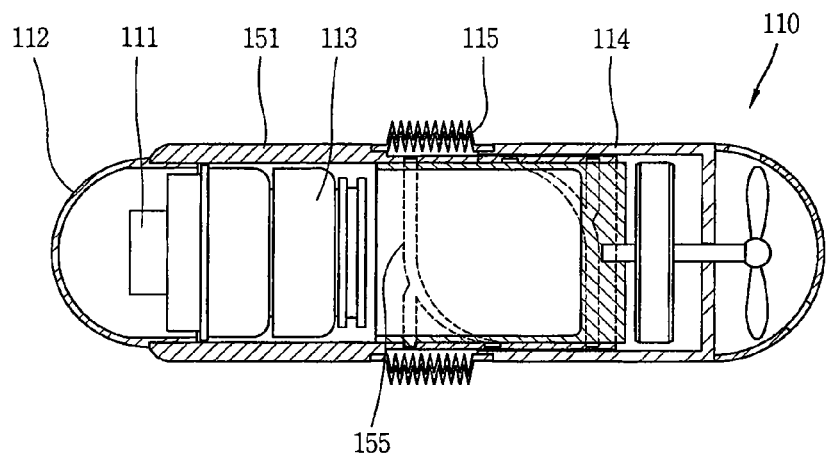
FIGS. 7a and 7b illustrate the operations of the endoscope of FIG. 5a which is swelled and reduced in volume.
Figure 7B:
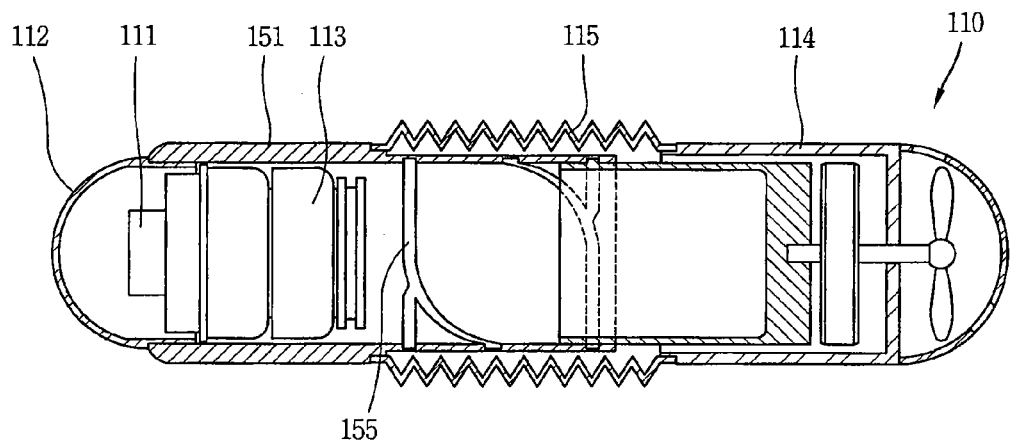

FIG. 6 is a conceptual view showing the principle of a kinetic conversion of a buoyancy control device of FIG. 5a, and FIGS. 7a and 7b illustrate the operations of the endoscope of FIG. 5a which is swelled and reduced in volume.

A protrusion pin 154 is formed to be protruded from an outer circumference of the second case 152. An insertion recess 155 in which the protrusion pin 154 is inserted is formed on an inner circumference of the first case 151.

The insertion recess 155 may be formed such that at least a portion thereof is sloped with respect to a rotational central axis of the second case 152. The insertion recess 155 includes first and second rotary recesses 155a and 155b and a connection recess 155c.

The first and second rotary recesses 155a and 155b are formed in a circumferential direction of the first case 151 to allow the protrusion pin 154 to be rotated continuously. For example, the first and second rotary recesses 155a and 155b have an annular shape without a disconnection. The first and second rotary recesses 155a and 155b are separately disposed.

The connection recess 155c connects the first and second rotary recesses 155a and 155b and is formed in a spiral direction. The connection recess 155c is sloped between the first and second rotary recesses 155a and 155b. The slope of the connection recess 155c may vary according to its fabrication method.

The portions where the first and second rotary recesses 155a and 155b and the connection recess 155c cross is formed to change a movement path of the protrusion pin 154 according to a rotation direction of the driving shaft 153a (See FIG. 5a). To this end, first and second protuberances 156a and 156b are formed at the crossings and protruded in the direction of the connection recess 155c from the first and second rotary recesses 155a and 155b.

The movement of the protrusion pin 154 according to the rotation of the driving shaft 153a and the operation of swelling and reducing the volume of the endoscope 110 will now be described.

In the present invention, the rotating of the driving shaft 153a toward the sloped direction of the connection recess 155c from the first rotary recess 155a will be called an increasing rotation, and the rotating of the driving shaft 153a in the direction opposite from the increasing rotation will be called a decreasing rotation.

When the driving shaft 153a is rotated in the direction of the decreasing rotation, the protrusion pin 154 is ceaselessly rotated along the first rotary recess 155a. At this time, the volume of the endoscope 110 is reduced to be the smallest.

When the driving shaft 153a is rotated in the direction of the increasing rotation, the protrusion pin 154 is moved from the first rotary recess 155a to the connection recess 155c by the first protuberance 156a. The protrusion pin 154 then moves in the direction of the second rotary recess 155b along the connection recess 155c. At this time, the insertion degree of the first and second cases 151 and 152 is reduced and the volume of the endoscope 110 increases.

When the protrusion pin 154 arrives at the second rotary recess 155b, the protrusion pin 154 is rotated ceaselessly. At this time, the volume of the endoscope 110 is the largest. As the volume increases, the buoyancy of the endoscope 110 increases, and the endoscope 110 can be moved in the direction opposite to the gravity within the fluid.

When the driving shaft 153a is rotated in the direction of decreasing rotation, the protrusion pin 154 is moved to the connection recess 155c from the second rotary recess 155b by the second protuberance 156b. The protrusion pin 154 is moved to the first rotary recess 155a along the connection recess 155c, and the volume of the endoscope 110 is then reduced.

Figure 8:
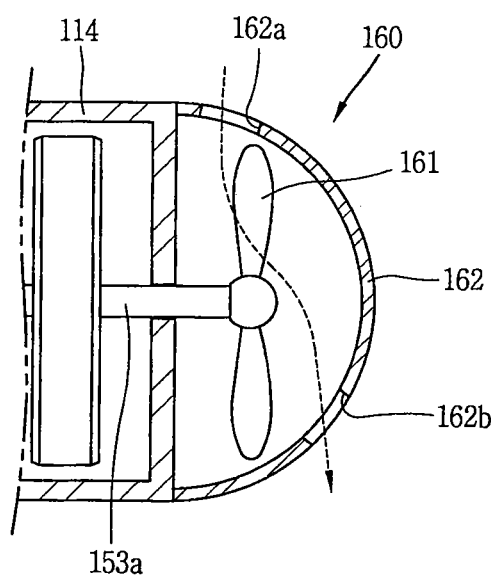

FIG. 8 is a conceptual view of an operation of a gyration device 160 of FIG. 5a.

With reference to FIG. 8, the gyration device 160 may be mounted in the main body of the endoscope 110. The gyration device 160 is formed to revolve the main body. The gyration device 160 may include a propelling unit 161 and a protection unit 162.

The propelling unit 161 is connected with the driving shaft 153a. The propelling unit 161 is formed to propel the main body through rotation. The propelling unit 161 may be, for example, a propeller or the like.

The protection unit 161 accommodates the propelling unit 161 therein, and is mounted on the third case 114. The protection unit 162 may have a net-like shape and protects the stomach walls against the protection unit 162.

The protection unit 162 includes a plurality of through holes 162a and 162b allowing the space in which the propelling unit 161 is installed to communicate with the outer side. The plurality of through holes 162a and 162b are disposed to be asymmetrical to the driving shaft 153a. For example, first and second through holes 162a and 162b may be formed with the propelling unit 161 interposed therebetween. The rotation of the propelling unit 161 makes a pressure difference in the direction of the rotational central axis. According to such pressure difference, water is introduced through the first through hole 162a and then discharged through the second through hole 162b.

Because the through holes 162a and 162b are disposed asymmetrically, the path of the water flow introduced into the propelling unit 161 is changed so that the water can be discharged from the propelling unit 161. As the path of the water flow is changed, the water flow applies a force to the main body in a direction perpendicular to the driving shaft 153a, and accordingly, the main body is revolved.

When the rotational speed of the propelling unit 161 is increased, the speed of the water flow increases to make the main body revolved in a wider range.

As so far described, according to the endoscope control method according to the exemplary embodiment of the present invention, with the water filled in the examination subject, the images of the stomach can be more precisely captured by controlling the buoyancy of the endoscope.

Also, the endoscope according to the exemplary embodiment of the present invention can be moved in the direction opposite to the gravity within the internal organ through the buoyancy control device. Thus, the images of the stomach having the large volume among the internal organs of the human beings or animals can be captured. In addition, the endoscope according to the exemplary embodiment of the present invention can be movable through the propelling unit and change its direction by means of the gyration device. Accordingly, the endoscope that can precisely capture images of the internal organ can be implemented.

Also, because the buoyancy is controlled by changing the volume of the main body of the endoscope, the examination subject can easily swallow the endoscope with a smaller volume. The volume of the main body of the endoscope is swelled in capturing images, and after the image capturing is finished, the endoscope with a small volume can be discharged to outside. Accordingly, the examination subject may feel less pain or no pain.

The endoscope system according to the exemplary embodiment of the present invention can capture the images of the internal organ more precisely with the controller which is remotely controlled and the chair controlled from a plurality of axes.

As the present invention may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. An endoscope comprising:
a main body including an image capturing unit for capturing image information, and configured in the form of a capsule; and
a buoyancy control device configured to control buoyancy by changing the volume of the main body,
wherein the buoyancy control device includes a driving shaft configured to rotate in an axial direction such that at least part of the main body moves to change the volume of the main body which changes through the rotation of the driving shaft.

2. The endoscope of claim 1, wherein the buoyancy control device comprises:
a driving unit configured to have the driving shaft; and
first and second cases connected to be relatively movable with each other according to the rotation of the driving shaft.

3. The endoscope of claim 1, wherein one of the first and second cases is inserted into another, the driving shaft is connected with the second case to allow the second case to be rotated, and the buoyancy control device is configured to change the rotation of the second case into a linear movement in a direction in which the first case is inserted.

4. The endoscope of claim 3, wherein a protrusion pin is formed on an outer circumference of the second case, an insertion recess into which the protrusion pin is inserted is formed on an inner circumference of the first case, and at least a portion of the insertion recess is sloped with respect to the rotational central axis of the second case.

5. The endoscope of claim 4, wherein the insertion recess comprises:
first and second rotary recesses formed in a circumferential direction of the first case to allow the protrusion pin to be rotated continuously, and disposed to be spaced apart; and
a connection recess connecting the first and second rotary recesses and formed in a spiral direction of the first case.

6. The endoscope of claim 5, wherein a portion where the first and second rotary recesses and the connection recess cross is formed to change a movement path of the protrusion pin according to the rotational direction of the driving shaft.

7. The endoscope of claim 1, further comprising:
a gyration device mounted at the main body and revolving the main body.

8. The endoscope of claim 7, wherein the buoyancy control device comprises a driving unit configured to have a driving shaft rotating in an axial direction, and
the gyration device comprises:
a propulsion unit connected to the driving shaft and propelling the main body through rotation; and
a protection unit accommodating the propulsion unit therein,
wherein the protection unit comprises a plurality of through holes connecting the space in which the propulsion unit is installed with the exterior, and disposed to be asymmetrical to the driving shaft.

9. An endoscope system comprising:
an endoscope and
a controller configured to control the endoscope,
wherein the endoscope comprises:
a main body including an image capturing unit for capturing image information, and configured in the form of a capsule; and
a buoyancy control device configured to control buoyancy by changing the volume of the main body,
wherein the buoyancy control device includes a driving shaft configured to rotate in an axial direction such that at least part of the main body moves to change the volume of the main body which changes through the rotation of the driving shaft.

10. The system of claim 9, further comprising:
a chair allowing an examination subject to sit thereon, and configured to be rotatable with respect to axes perpendicular to each other.

11. The system of claim 9, further comprising:
a reception pad configured to receive a signal transmitted from the endoscope, and attached to a front surface and a rear surface of the examination subject.

* * * * *